(12) United States Patent
Yoon

(10) Patent No.: US 7,541,431 B2
(45) Date of Patent: Jun. 2, 2009

(54) CRISTIN/R-SPONDIN LIGANDS ACTIVE IN THE WNT SIGNALING PATHWAY AND METHODS, COMPOSITIONS AND KITS RELATING THERETO

(75) Inventor: Jeong Kyo Yoon, Falmouth, ME (US)

(73) Assignee: Maine Medical Center, Scarborough, MA (US)

( * ) Notice: Subject to any disclaimer, the term of this patent is extended or adjusted under 35 U.S.C. 154(b) by 131 days.

(21) Appl. No.: 11/505,511

(22) Filed: Aug. 17, 2006

(65) Prior Publication Data

US 2007/0059829 A1 Mar. 15, 2007

Related U.S. Application Data

(60) Provisional application No. 60/714,955, filed on Sep. 7, 2005.

(51) Int. Cl.
*C07K 14/435* (2006.01)
*C07K 14/475* (2006.01)
(52) U.S. Cl. .......................... 530/350; 514/12; 435/377
(58) Field of Classification Search ........................ None
See application file for complete search history.

(56) References Cited

U.S. PATENT DOCUMENTS

| 5,605,793 | A | 2/1997 | Stemmer et al. | |
|---|---|---|---|---|
| 6,537,776 | B1 | 3/2003 | Short | |
| 6,824,973 | B2 * | 11/2004 | Tang et al. | 435/4 |

FOREIGN PATENT DOCUMENTS

WO   WO 01/77169 A2   10/2001

OTHER PUBLICATIONS

Kim et al., Science Aug. 19, 2005: vol. 309. No. 5738, pp. 1256-1259.*
Berger, W., et al. (1992) Nat Genet 1:199-203.
Chen, Z.Y., et al. (1992) Nat Genet 1:204-208.
Willert, K., et al. (2003) Nature 423:448-452.
Semenov, M.V., et al. (2001) Curr Biol 11:951-961.
Polakis, P. (2000) Genes Dev 14:1837-1851.
He, X., et al. (2004) Development 131:1663-1677.
Kuhl, M., (2004) Front Biosci 9:967-974.
Xu, Q., et al. (2004) Cell 116:883-895.
Inoue, T., et al. (2004) Cell 118:795-806.
Yoon, J.K., and Wold, B. (2000) Genes Dev 14:3204-3214.
Yoon, J.K., Moon, R.T., and Wold, B. (2000) Dev Biol 222:376-391.
Kamata, T., et al. (2004) Biochim Biophys Acta 1676:51-62.
Kazanskaya, O., et al. (2004) Dev Cell 7, 525-534.
Adams, J.C., and Tucker, R.P. (2000) Dev Dyn 218:280-299.
Fernig, D.G., and Gallagher, J.T. (1994) Prog Growth Factor Res 5:353-377.
Takada, S., et al. (1994) Genes Dev 8:174-189.
Brigstock, D.R. (2003) J Endocrinol 178:169-175.
Mercurio, S., et al. (2004) Development 131:2137-2147.
Latinkic, B.V., et al. (2003) Development 130:2429-2441.
Glinka, A., et al. (1998) Nature 391:357-362.
Mao, B., et al. (2002) Nature 417:664-667.
Subramanian, V., Meyer, B.I., and Gruss, P. (1995) Cell 83:641-653.
Wilkinson, D.G., Bhatt, S., and Herrmann, B.G. (1990) Nature 343:657-659.
Hsieh, J.C., et al. (1999) Proc Natl Acad Sci USA 96:3546-3551.
Tamai, K., et al. (2000) Nature 407:530-535.

* cited by examiner

*Primary Examiner*—David S Romeo
*Assistant Examiner*—Daniel C Gamett
(74) *Attorney, Agent, or Firm*—Pierce Atwood LLP; Kevin M. Farrell; David J. Wilson

(57) ABSTRACT

The present invention relates to compositions and method for the modulation of Wnt pathway signaling. The Wnt signaling pathway is instrumental in the regulation of cell proliferation, differentiation and morphogenesis.

8 Claims, 11 Drawing Sheets

| Gene | Human | Mouse | # of Exons (H/M) |
|---|---|---|---|
| Cristin1/R-spondin3 | Chr. 6q22 | Chr. 10B5 | 5/5 |
| Cristin2/R-spondin2 | Chr. 8q23 | Chr. 15B3 | 6/6 |
| Cristin3/R-spondin1 | Chr. 1p34 | Chr. 4D2 | 8*/6 |
| Cristin4/R-spondin4 | Chr. 20p13 | Chr. 2G3 | 5/5 |

CRISTIN/R-SPONDIN LIGANDS ACTIVE IN THE WNT SIGNALING PATHWAY AND METHODS, COMPOSITIONS AND KITS RELATING THERETO

FIELD OF THE INVENTION

The present invention relates to the finding that the Cristin/R-spondin family of heparin-binding proteins function as Fzd8/LRP6 receptors and induce β-catenin/TCF-dependent gene activation via the Wnt signaling pathway.

BACKGROUND

Wnt signaling is one of the key signaling pathways that governs many aspects of normal development including limb development, body axis extension, CNS development and kidney development by controlling cell proliferation, differentiation and migration (Berger, W., et al. (1992) *Nat Genet* 1:199-203; Chen, Z. Y., et al. (1992) *Nat Genet* 1:204-208; Willert, K., et al. (2003) *Nature* 423:448-452; Semenov, M. V., et al. (2001) *Curr Biol* 11:951-961). Wnt signaling is also known to play important roles in homeostasis of adult tissue. For example, deregulation of Wnt signaling, usually an aberrant activation, is highly associated with several forms of cancer in humans (Polakis, P. (2000) *Genes Dev* 14:1837-1851; He, X., et al. (2004) *Development* 131:1663-1677). More recently, Wnt signaling has been implicated in maintaining the self-renewal capacity of embryonic and hematopoietic stem cells, or inducing neural fate differentiation of neural stem cells (Kuhl, M. (2004) *Front Biosci* 9:967-974; Xu, Q., et al. (2004) *Cell* 116:883-895; Inoue, T., et al. (2004) *Cell* 118:795-806, Yoon, J. K., and Wold, B. (2000) *Genes Dev* 14:3204-3214). Over the last two decades since the first Wnt ligand was identified (Yoon, J. K., Moon, R. T., and Wold, B. (2000) *Dev Biol* 222:376-391; Kamata, T., et al. (2004) *Biochim Biophys Acta* 1676:51-62), significant progress has been made in identifying key signaling components including the receptors, and determining their roles in the Wnt signaling pathway (Kazanskaya, O., et al. (2004) *Dev Cell* 7, 525-534; Adams, J. C., and Tucker, R. P. (2000) *Dev Dyn* 218:280-299; Fernig, D. G., and Gallagher, J. T. (1994) *Prog Growth Factor Res* 5:353-377; Takada, S., et al. (1994) *Genes Dev* 8:174-189). Numerous studies suggest that Wnt signaling is regulated at various levels of the signaling axis either positively or negatively and a sum of positive and negative regulation determines the strength and activity of Wnt signaling at a given time and location in a certain biological system. Therefore, identifying these regulators and elucidating their regulatory mechanisms that affect Wnt signaling is of critical importance to this field. Better understanding of these regulators is worthwhile considering the potential impact on the design and development of diagnostic and/or therapeutic tools for the diseases associated with Wnt signaling in humans.

Therefore, what is needed are both nucleotide sequences and the encoded proteins that can be used to 1) better understand the biochemistry involved in the regulation of such critical physiological pathways and, 2) for the treatment of disease states that result from the misregulation of the Wnt signaling pathway.

SUMMARY OF THE INVENTION

The present invention relates to novel nucleotide sequences and the proteins encoded therein. The novel nucleotide sequences and proteins play a role in the Wnt signaling pathway. The Wnt signaling pathway is one of the key pathways in controlling cell proliferation, differentiation and morphogenesis. Breakdown of this pathway results in various disease states including tumorigenesis. The nucleotide sequences of the present invention encode a novel protein named Cristin1/R-spondin3. Cristin1/R-spondin3 is a cysteine-rich, secreted protein with an affinity to heparin. Although the present invention is not limited by theory or mechanism in any way, these proteins have been shown in the present invention to function as Frizzled/LRP6 receptor ligands and to induce the canonical Wnt/β-catenin signal pathway leading to TCF-dependent gene activation.

DETAILED DESCRIPTION OF THE INVENTION

Figure 1:
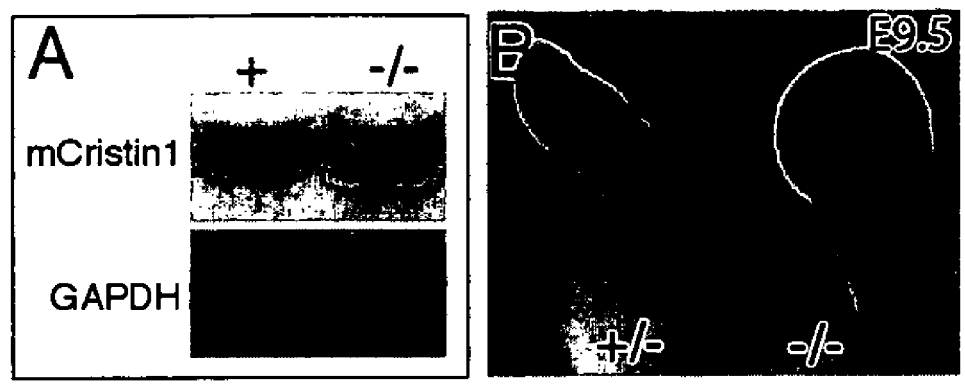
FIG. 1 shows that the multi-gene family proteins Cristins/R-spondins are novel secreted proteins: (A) RT-PCR, (B) whole mount in situ hybridization. (C) Comparison of mouse Cristin/R-spondin family protein sequences R-spondin3 [SEQ ID NO: 1], R-spondin2 [SEQ ID NO: 2], R-spondin1 [SEQ ID NO: 3] and R-spondin4 [SEQ ID NO: 4]. (D) Phylogenic analysis of vertebrate R-spondin family proteins. (E) Syntenic relationship between human and mouse R-spondin gene loci.
Figure 1:
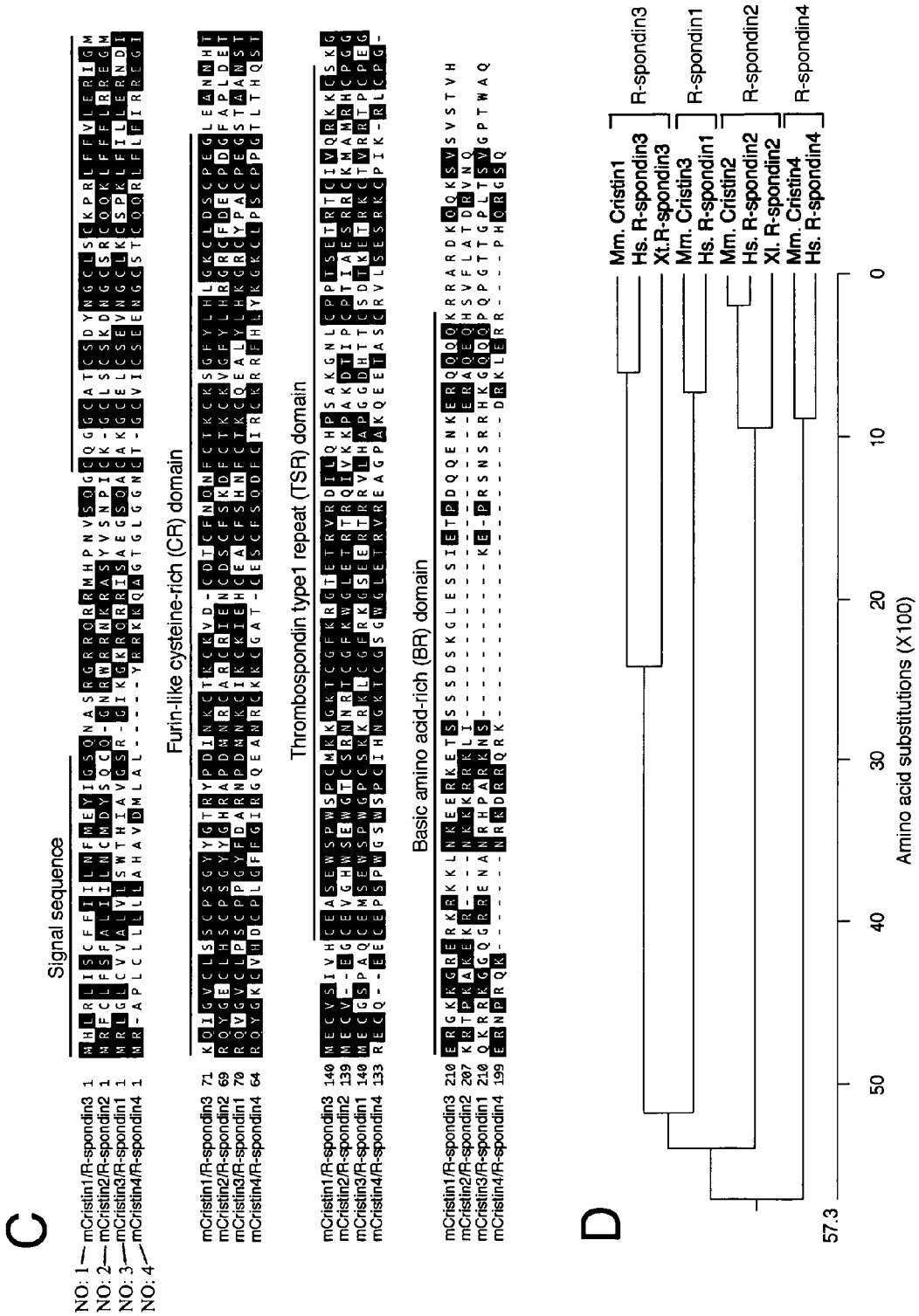

The following definitions are provided to clarify, not limit, the present invention.

The term "isolated" shall refer to a polynucleotide, a polypeptide, an antibody, or a host cell that is in an environment different from that in which the polynucleotide, the polypeptide, the antibody, or the host cell naturally occurs. An isolated polynucleotide, polypeptide, antibody, or host cell is generally substantially purified.

The present invention is based on the finding that the Cristin/R-spondin family of heparin-binding proteins function as Fzd8/LRP6 receptor ligands and induce β-catenin/TCF-dependent gene activation. The present invention also provides evidence that Cristin/R-spondin proteins positively modulate Wnt ligand activity. As described in the Exemplification section that follows, Cristin1 (R-spondin3) is shown to be a novel ligand for the Fzd8/LRP6 receptor complex that functions by intracellularly transducing signals that stabilize β-catenin in the cytoplasm followed by activation of gene transcription in the nucleus. The findings expand the current view of Wnt signaling and implicate the presence of active β-catenin signaling through the Fzd/LRP receptor complexes in a Wnt-free biological context.

The present invention relates, in one aspect, to a method for activating Wnt/β-catenin signaling. In this method a cell in which activation of Wnt/β-catenin signaling is desired is contacted with an exogenous agent having an amino acid sequence with at least 70% or, more preferably, at least 90% identity to the Cristin1/R-spondin3 amino acid sequence of SEQ ID NO: 1, wherein the percent identity is over the entire length of the amino acid sequences aligned for comparison purposes. In one aspect the exogenous agent comprises SEQ ID NO: 1 or a homolog thereof. The term "agent" as used herein is intended to refer to a protein, polypeptide, peptide, mimetic, or a hybrid of any of the same.

Contact of the cell is to be performed using an amount of exogenous agent and for a sufficient duration to result in a detectable enhancement of β-catenin protein stability in the cell and induction of β-catenin/TCF-dependent gene expression. Enhancement of β-catenin stability in the cell may be determined directly by assaying levels of steady-state β-catenin protein such as by immunohistochemical methods such as outlined in the Exemplification section that follows. An immunoblotting assay may be employed for this purpose. In such an assay, enhanced stabilization is measured as decreased degradation of β-catenin, which is measured by assessing the ability of an antibody directed against β-catenin to immunoblot full-length β-catenin from cell lysates from cells cultured in the presence and absence of the exogenous agent. For example, mammalian cells that express β-catenin may be homogenized in the presence and absence of the exogenous agent. An antibody directed against β-catenin is used in immunoblotting analysis of the cell homogenate to evaluate the level of full-length β-catenin. In general, an exogenous agent should increase the level of β-catenin protein by at least 20%, more preferably at least 100% and most preferably at least 1000% in the context of the present invention. In some instances of the present invention, the level of increase in β-catenin protein level is greater than at least 1000% but less than about 20,000%. Enhancement of β-catenin stability may also be detected indirectly, such as based on a detection of cellular differentiation with appropriate markers. An increase in β-catenin protein levels is indicative of enhancement of β-catenin protein stability. Induction of β-catenin/TCF-dependent gene expression may be similarly determined.

Induction of β-catenin/TCF-dependent gene expression may be detected by an activation of expression of reporter gene wherein multiple TCF binding sites are inserted in front of the reporter gene-encoding enzyme such as luciferase. An increase of reporter activity is indicative of β-catenin/TCF-dependent gene activation.

Because the therapeutic target of the present invention is extracellular, treatment with an exogenous agent of the present invention is an attractive therapeutic option for modulating β-catenin/TCF activity and other downstream targets of Fzd8/LRP6 receptor complex activation. It is therefore not a requirement that the exogenous agent of the present invention be delivered intracellularly, thereby overcoming this pharmaceutical challenge. An exogenous agent need only be delivered to the extracellular surface of Wnt-responsive cells for the treatment to be effective.

One skilled in the art will recognize that a biologically active fragment of Cristin1/R-spondin3 may be used in lieu of the full-length sequence or sequences in the context of the present invention. A "biologically active fragment" is intended to encompass any analogue, mimetic, truncation, deletion and/or substitution of full-length Cristin1/R-spondin3 with the ability to activate Wnt signaling in the methods of the present invention. A biologically active fragment may further be a protein, polypeptide or peptide. Peptidomimetics of Cristin1/R-spondin3 and Cristin1/R-spondin3 domains may be designed computationally using structural data, as is known in the art. Additionally, in one embodiment of the present invention, it is contemplated that analogs and mutations of the nucleotide sequence of Cristin1/R-spondin3 or of the Cristin1/R-spondin3 protein may be generated by directed molecular evolution. The techniques of directed molecular evolution are known in the art (see, for example, U.S. Pat. No. 5,605,793 to Stemmer, et al., or U.S. Pat. No. 6,537,776 to Short, which are incorporated herein by reference). The proteins generated by directed molecular evolution will have a lesser, greater or equal ability to activate the Wnt signaling pathway as Cristin1/R-spondin3.

The methods disclosed herein for activating Wnt signaling cell may be carried out in vivo or in vitro. Activation of Wnt signaling may be effectively achieved in a Wnt-responsive cell in tissue culture. Wnt signaling is conserved in vertebrates and invertebrates and, as such, methods for activating the same may be carried out in tissue culture cells derived from either vertebrates or nonvertebrates. Examples of vertebrate cell lineages in which Wnt signaling is conserved include human, mouse, Xenopus, chicken and zebrafish. Examples of invertebrate cell lineages in which Wnt signaling is conserved include C. elegans and Drosophila. The methods disclosed herein for activating Wnt signaling may be used to study Wnt signaling or for the development of therapeutics for treating diseases associated with aberrant Wnt signaling. The methods of the present invention are not intended to be limited only for use with cells in culture but may also be used in animal models and patients.

Methods of the present invention for activating Wnt signaling in a Wnt-responsive cell may also be carried out in vivo. Activation of Wnt signaling may be effectively achieved in cells within a human or non-human animal. Since Wnt signaling is conserved in vertebrates and invertebrates, the methods of the present invention may be used to effect Wnt signaling in vertebrates such as human, mouse, *Xenopus*, chicken, and zebrafish and invertebrates such as *C. elegans* and *Drosophila*. In vivo, the methods of the present invention may be used to alter cell fate decisions in a developing or mature animal.

In an embodiment of the present invention, the cell may be further contacted with Wnt ligand in addition to the exogenous agent as described above. In the Exemplification section that follows, evidence that Cristin/R-spondin plays a positive modulatory role in Wnt ligand activity is provided. When a cell is contacted with both Wnt and Cristin/R-spondin, the signaling activity is significantly higher than when a similar cell is contacted with either Wnt or Cristin/R-spondin alone. Wnt and Cristin/R-spondin therefore act synergistically in inducing of β-catenin/TCF-dependent gene expression. In preferred embodiments, where a cell is contacted with both a Wnt ligand and the exogenous agent, the Wnt ligand is Wnt1 or Wnt3a.

In another aspect, the invention relates to an isolated agent having an amino acid sequence with at least 70%, or more preferably at least 90%, identity to the Cristin1/R-spondin3 amino acid sequence of SEQ ID NO: 1. Additionally, in another aspect, the present invention contemplates that both the RNA and DNA nucleotide sequences capable of encoding SEQ ID NO: 1 are also embodiments of the present invention. It is within the skill of the art to determine all the RNA and DNA sequences capable of encoding the amino acid sequence of SEQ ID NO: 1 due to the redundancy of the genetic code.

In one aspect the exogenous agent comprises the amino acid sequence of SEQ ID NO: 1 or a homolog thereof. The homolog may be a Cristin1/R-spondin3 homolog of any species in which Wnt signaling is conserved. Examples such species include murine, chicken, *Xenopus*, zebrafish, and human. Compositions containing the isolated agent are within the scope of the present invention. Such compositions may include Wnt protein such as Wnt1 or Wnt3a.

A Wnt-responsive cell, either in vitro or in vivo, may be contacted directly with a composition of the present invention under conditions sufficient to bind the exogenous agent to the Fzd8/LRP6 receptor complex. The Wnt-responsive cell may express the exogenous agent from an introduced exogenous construct harboring an expressible cDNA. If the composition includes either an exogenous LRP6, Frizzled family and/or Wnt ligand, the LRP5/6, Frizzled receptor family ligand may also be expressed from an introduced exogenous construct harboring the appropriate expressible cDNA or cDNAs. In both non-human and human animals, the construct or constructs may be delivered by methods of gene therapy, which are known in the art. Alternatively, the composition may be delivered to a cell indirectly by increasing the expression of an endogenous Cristin1/R-spondin3 gene or endogenous Cristin1/R-spondin3, Wnt, Frizzled family and/or LRP6 genes. The composition may be delivered to a cell or cells as expressible RNAs by injection or other delivery means as is known in the art.

In yet another aspect, the present invention relates to an isolated nucleotide sequence that encodes a protein having an amino acid sequence with at least 70%, or more preferably at least 90%, identity to the Cristin1/R-spondin3 amino acid sequence of SEQ ID NO: 1. In one aspect the isolated nucleotide sequence encodes the amino acid sequence of SEQ ID NO: 1 or a homolog thereof. The homolog may be a Cristin1/R-spondin3 homolog of any species in which Wnt signaling is conserved. Examples such species include murine, chicken, *Xenopus*, zebrafish, and human. The isolated nucleotide sequence may be identical to, or substantially identical to, SEQ ID NO: 1. Compositions containing the isolated nucleotide sequence are also within the scope of the present invention. Such compositions may include an isolated Wnt protein such as Wnt1 or Wnt3a, or isolated nucleotide sequences encoding the same. Additionally, in one embodiment of the present invention, it is contemplated that analogs and mutations of the nucleotide sequence of Cristin1/R-spondin3 may be generated by directed molecular evolution or as the by-product of directed molecular evolution when employed to develop variants of Cristin1/R-spondin3. The techniques of directed molecular evolution are known in the art (see, for example, U.S. Pat. No. 5,605,793 to Stemmer, et al., or U.S. Pat. No. 6,537,776 to Short, which are incorporated herein by reference).

In yet another aspect, the present invention relates to an expression vector that encodes a protein having an amino acid sequence with at least 70%, or more preferably at least 90%, identity to the Cristin1/R-spondin3 amino acid sequence of SEQ ID NO: 1. In one aspect the expression vector contains a nucleotide sequence that encodes the amino acid sequence of SEQ ID NO: 1 or a homolog thereof. The homolog may be a Cristin1/R-spondin3 homolog of any species in which Wnt signaling is conserved. Examples such species include murine, chicken, *Xenopus*, zebrafish and human. The included nucleotide sequence may be identical to, or substantially identical to, SEQ ID NO: 1. Compositions containing the expression vector are also within the scope of the present invention. Such compositions may include an isolated LRP6 and/or Wnt protein such as Wnt1 or Wnt3a, or an expression vector or vectors encoding the same.

In another aspect, the invention relates to a cell which exogenously expresses a protein having an amino acid sequence with at least 70%, or more preferably at least 90%, identity to the Cristin1/R-spondin3 amino acid sequence of SEQ ID NO: 1, wherein the percent identity is over the entire length of the amino acid sequences aligned for comparison purposes. In one aspect the cell exogenously expresses a protein having the amino acid sequence of SEQ ID NO: 1 or a homolog thereof. The homolog may be a Cristin1/R-spondin3 homolog of any species in which Wnt signaling is conserved. Examples such species include murine, chicken, *Xenopus*, zebrafish and human. The cell may additionally exogenously express an LRP6 and/or Wnt protein such as Wnt1 or Wnt3a.

It is an object of the present invention to employ the methods disclosed herein for modulating cellular responses to Wnt signaling. Wnt signaling is one of the key signaling pathways that governs many aspects of normal development, including body axis extension and CNS and kidney development. Activation of Wnt signaling is known to stimulate cellular proliferation, differentiation, and migration. Wnt signaling is also known to play important roles in tumorigenesis, homeostasis of adult tissue as well as maintaining the self-renewal capacity of embryonic and hematopoietic stem cells and inducing neural fate differentiation of neural stem cells. Methods of the present invention may be used to effect any of the above processes or downstream events resulting from the same.

Thus the methods provided herein may be useful for the treatment of a disorder modulated by TCF/β-catenin dependent gene activation. Practical applications of the present invention include controlling growth of stem cells without differentiation. The methods of the present invention may also be used therapeutically to treat disorders correlated with defective Wnt signaling. The methods of the present invention may be specifically used to treat individuals with a mutation in the Wnt co-receptor LRP5/6 for treating osteoporosis. In this role, the methods may be used to enhance bone differentiation.

A composition of the present invention may be administered to an animal in a physiological carrier in a therapeutically effective amount. Such compositions may be administered alone or in combination with other therapies and may be delivered intravenously, subcutaneously or orally to the animal. Administration may be systemic or local.

While specific embodiments of the present invention have been described, it will be apparent to those skilled in the art that various modifications thereto can be made without departing from the spirit or the scope of the invention as defined in the examples and appended claims.

EXPERIMENTAL

Materials and Methods

Plasmid DNA Constructs

Mouse EST cDNA clones encoding full-length Cristins/R-spondins were obtained from the I.M.A.G.E. consortium. The coding regions of all Cristins/R-spondins and the deletion mutants of Cristin1/R-spondin3 were PCR amplified and cloned into pcDNA3 plasmid carrying a C-terminal hemagglutinin (HA) tag (pcDNA3-HA) or Myc-His epitope tags (pcDNA3.1-MycHis). The coding sequence of mouse Wnt1 was PCR amplified and cloned into both pcDNA3-HA and CS2+MT to create HA- and Myc-tagged constructs, respectively.

Cell Culture, DNA Transfection, and Luciferase Assay

Human embryonic kidney 293T and mouse L-cells were routinely maintained in Dulbecco's modified eagle medium (DMEM) containing 10% fetal bovine serum (FBS) in 5% $CO_2$ at 37° C. P19 cells were maintained in minimum essential medium (MEM) supplemented with 7.5% calf serum and 2.5% FBS. 293T cells were transfected using FuGene6 reagent (Roche) according to the manufacturer's protocol. For luciferase assay, $3\times10^4$ cells were seeded in each well of 24-well plates. TopFlash or FopFlash reporter (20 ng), and Renilla luciferase construct (RL-TK, 10 ng) were used along with various amounts of expression plasmids, as indicated in the figure legends. Both luciferase activities were measured by using a dual luciferase assay kit (Promega), according to the manufacturer's protocol.

Preparation of Conditioned Media (CM), and Isolation of Cristin/R-Spondin Proteins Wnt3a CM was prepared from the mouse Wnt3a L-cell line (obtained from ATCC), as described previously (Willert, K., et al. (2003) *Nature* 423:448-452). CM containing Cristins/R-spondins were obtained from 293T cells transiently transfected with Cristin/R-spondin expression plasmids. For biochemical assay, DMEM: F-12 (1:1) serum-free medium was used to obtain the CM. Soluble heparin was added to the culture media at the concentration of 50 µg/ml. DMEM-10% FBS medium was used to prepare the CM for biological assays including the luciferase and β-catenin stabilization assays. For purification of histidine-tagged Cristin/R-spondin proteins, total lysates of 293T cells transiently transfected with histidine-tagged Cristin/R-spondin expression constructs were prepared with lysis buffer (50 mM Tris, pH 8.0, 150 mM NaCl, 0.1% NP-40) containing protease inhibitor cocktail V (Calbiochem). The cell lysates were incubated with Ni-NTA agarose beads (Qiagen) for 2 hrs at 4° C., and washed with 10 mM imidazole buffer three times. The Cristin/R-spondin proteins were eluted with buffer containing 250 mM imidazole. Human IgG fusion proteins were prepared as serum-free CM formats from the transiently transfected 293T cells, as described previously (Semenov, M. V., et al. (2001) *Curr Biol* 11:951-961).

Heparin Binding and Cristin/R-spondin Binding Assay

Total cell lysates of 293T cells transfected with Cristin-HA constructs were prepared using lysis buffer (50 mM Tris, pH8.0, 150 mM NaCl, 0.1% NP-40) containing protease inhibitors, and incubated with heparin-sepharose beads (Sigma) at 4° C. overnight. The beads were washed with the lysis buffer three times at room temperature, and the Cristin/R-spondin proteins were eluted with buffers with increasing NaCl concentrations. The presence of Cristin proteins in each eluted fraction was determined by western blot analysis.

CM containing IgG, Fzd8CRD-IgG and LRP6N-IgG were first incubated with protein A-sepharose beads to conjugate IgG fusion proteins to the beads. Histidine-tagged Cristin/R-spondin proteins were incubated with the beads at 4° C. overnight. After three washings with PBS, associated Cristin/R-spondin proteins were analyzed by western blot analysis using anti-His or anti-Myc primary antibodies. The filters were reprobed with anti-human IgG Fc antibodies.

RNA Isolation and RT-PCR

Total RNA was isolated from cultured cells and *Xenopus* animal cap explants using TRIzol reagent (Invitrogen), according to the protocol provided by manufacturer, and digested with RNase-free DNase I to remove genomic DNA contamination. First strand cDNA was synthesized with SuperScriptII (Invitrogen), and 1/10 of the cDNA was routinely used for each PCR reaction. The sequences of PCR primers as follows: mouse GAPDH (sense, 5'-GTG-GCAAAGTGGAGATTGTTGCC-3' [SEQ ID NO: 5] and antisense, 5'-GATGATGACCCGTTTGGCTCC-3' [SEQ ID NO: 6]); mouse Cristin1/R-spondin3 (sense, 5'-GTACACT-GTGAGGCCAGTGAA-3' [SEQ ID NO: 7] and antisense, 5'-ATGGCTAGAACACCTGTCCTG-3' [SEQ ID NO: 8]); mouse BrachyuryT (sense, 5'-TGCTGCCTGTGAGT-CATAC-3' [SEQ ID NO: 9] and antisense, 5'-ACAAGAG-GCTGTAGAACATG-3' [SEQ ID NO: 10]); mouse Cdx1 (sense, 5'-GAACCAAGGACAAGTACCGTG-3' [SEQ ID NO: 11] and antisense, 5'-GGTAGAAACTCCTCCT-TGACG-3' [SEQ ID NO: 12]); *Xenopus* Siamois (sense, 5'-AAGGAACCCCACCAGGATAA-3' [SEQ ID NO: 13] and antisense, 5'-TACTGGTGGCTGGAGAAATA-3' [SEQ ID NO: 14]); *Xenopus* Xnr3 (sense, 5'-TCCACTTGTG-CAGTTCCACAG-3' [SEQ ID NO: 15] and antisense, 5'-ATCTCTTCATGGTGCCTCAGG-3' [SEQ ID NO: 16]); and *Xenopus* XMax2 (sense, 5'-GTGGAAAGCGACGAA-GACTC-3' [SEQ ID NO: 17] and antisense, 5'-CCGAGCTC-GAGTAGTTGGAC-3' [SEQ ID NO: 18]).

Western Blot, Immunoprecipitation and Immunofluorescent Staining

For western blot, anti-HA (12CA5), anti-Myc (9E10), anti-His (Rockland) and anti-human Fc (Jackson Immunoresearch) antibodies were used in 1:2000, 1:5,000, 1:3,000, and 1:4,000 dilutions, respectively. Anti-β-catenin antibodies (Pharmingen) and anti-β-actin (Sigma) were used at 1:500 and 1:5,000 dilutions, respectively. Target proteins were detected by the chemiluminescent method (Amersham). For immunoprecipitation, Protein-A sepharose and anti-HA or Myc antibodies conjugated to agarose (Sigma) or sepharose (Santa Cruz) beads were used to purify the protein complex. Subcellular localization of Cristin/R-spondin proteins in 293T cells was determined by immunofluorescent-staining using mouse anti-HA primary antibodies (1:1,000), and goat anti-mouse IgG secondary antibodies conjugated with Alexa 488 (1:500, Molecular Probes). Images were acquired using a Leica confocal microscope.

Mouse Embryo Collection and Whole-mount in Situ Hybridization

Wild-type embryos in different embryonic stages were collected from timed matings of ICR mice. The pMesogenin1 mutant embryos were collected from the mating between heterozygous animals; and the genotypes of collected embryos were determined by genomic DNA PCR with yolk sac DNA as previously described (Yoon, J. K., and Wold, B. (2000) Genes Dev 14:3204-3214). The collected embryos were immediately fixed in freshly prepared 4% paraformaldehyde-PBS solution overnight at 4° C., and kept in 100% methanol at −20° C. until use. Digoxygenin-labelled antisense Cristin1/R-spondin3 RNA probes were in vitro synthesized from a linearized DNA template by using appropriate RNA polymerases in the presence of Digoxygenin-CTP. Whole-mount in situ hybridization was performed as previously described (Yoon, J. K., and Wold, B. (2000) Genes Dev 14:3204-3214). Photography of stained embryos was accomplished using a Zeiss AxioCam digital camera.

Xenopus Embryos and Animal Cap Explants

Xenopus embryos were prepared by in vitro fertilization of oocytes collected from hormonally induced females by standard protocol. Capped RNA was synthesized using a Ambion Message Machine kit according to the provided protocol. Various amounts of RNA were injected into the animal pole of 2-cell stage embryos. Animal caps were explanted at the blastula stage and cultured in 1× Modified Bart's Saline (MBS) until the companion embryos reached gastrulation stage.

RESULTS

Mouse Cristin/R-spondin is a Multi-gene Family of Novel Secreted Protein

It was previously demonstrated that mouse mutants lacking the pMesogenin1 gene, which encodes a presomitic mesoderm (PSM)-specific basic helix-loop-helix (bHLH) transcription factor (Yoon, J. K., Moon, R. T., and Wold, B. (2000) Dev Biol 222:376-391), display severe defects in posterior paraxial mesoderm development (Yoon, J. K., and Wold, B. (2000) Genes Dev 14:3204-3214). In an attempt to understand the molecular mechanisms by which pMesogenin1 regulates paraxial mesoderm development, potential target genes for pMesogenin1 were screened by analyzing gene expression profiles in the PSM of pMesogenin1 null and wild-type embryos. One gene, whose RNA expression was increased approximately 4-fold in the pMesogenin1 null mutant samples, encoded a novel secreted protein (FIG. 1A). Based on the protein structure derived from the predicted peptide sequences, this gene was named, Cristin1(Cysteine-rich and single thrombospondin domain containing protein 1) (FIG. 1C). Whole-mount in situ hybridization analysis showed prominent RNA expression of Cristin1/R-spondin3 in tailbud of wild-type mouse embryos (FIG. 1B). Consistent with RT-PCR data, Cristin1/R-spondin3 expression within the tailbud of pMesogenin1 homozygous null mutants was significantly expanded, increased, and tightly associated with the tailbud defects. Thus, aberrant Cristin1/R-spondin3 expression may be related to the pMesogenin1 null phenotype. Cristin1/R-spondin3 expression was also detected in the primitive streak, dorsal neural tube, forebrain, and migrating neural crests of mouse embryos (data not shown, detailed expression studies will be published elsewhere). In searching sequence databases, three genes were identified that were homologous to Cristin1/R-spondin3 in the mouse genome (designated Cristin 2, 3, and 4, FIG. 1C). Four homologous genes were also identified in the human genome, as well as EST clones with high sequence homology among other vertebrates including chicken, Xenopus, and zebrafish. Phylogenetic analysis of predicted protein sequences, syntenic relationships of gene loci in human and mouse chromosomes, and comparisons of genomic structures determined the orthologous relationships among the human and mouse genes (FIG. 1D and E). Interestingly, searches of the Drosophila and C. elegans genome databases failed to identify Cristin homologs. Thus, Cristin genes may be unique to vertebrates, although functional homologs may exist in invertebrate species. Recently, the isolation of mouse R-spondin, which is identical to mouse Cristin3, and two Xenopus homologs of the mouse R-spondin genes were reported (Kamata, T., et al. (2004) Biochim Biophys Acta 1676:51-62; Kazanskaya, O., et al. (2004) Dev Cell 7:525-534). Thus, for consistency in nomenclature, the Cristin genes were renamed as R-spondins as indicated in FIG. 1C.

Comparisons of the predicted mouse R-spondin amino acid sequences revealed significant homologies (FIG. 1C). First, all R-spondin proteins contain an N-terminal 20 to 25 amino acid hydrophobic region, which likely serves as a signal sequence for secretion. Three additional conserved protein domains are also evident: (i) a cysteine-rich (CR) domain with homology to the cysteine-rich domain of Furin and the insulin-like growth factor receptor (IGFR); (ii) a Thrombospondin Type I repeat (TSR) (Adams, J. C., and Tucker, R. P. (2000) Dev Dyn 218:280-299); and (iii) a C-terminal basic amino acid-rich (BR) domain (FIG. 1C).

Figure 2:
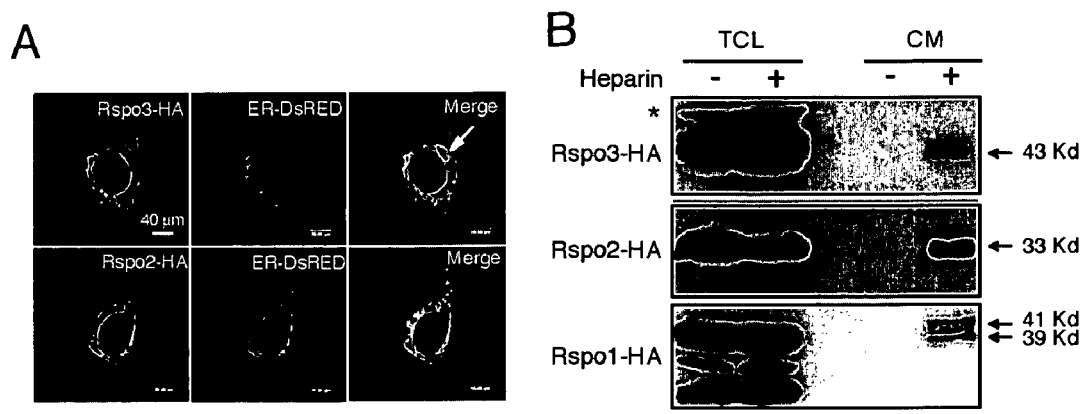
FIG. 2 shows the R-spondins are secreted proteins. (A) Mouse R-spondins are localized in the endoplasmic reticulum and Golgi apparatus in 293T cells. (B) Western blots of cell medium after culture of 293T cells with expression constructs encoding HA-tagged R-spondins.

The presence of a putative signal sequence and the lack of a notable transmembrane domain suggest that R-spondins may be secreted proteins. To test this possibility, expression plasmids encoding HA-tagged R-spondins were transfected into 293T human embryonic kidney cells, and examined subcellular localization of R-spondins by immunofluorescent staining. R-spondin proteins were mainly detected within the endoplasmic reticulum as well as the Golgi apparatus (FIG. 2A), indicating that R-spondin proteins are in the secretory pathway. In similarly transfected cells, the expression and secretion of R-spondin proteins into the CM was monitored by western blotting. The majority of the R-spondin proteins was associated with total cell lysates, and was not detected in the CM (FIG. 2B). Interestingly, the addition of soluble heparin to the culture medium significantly enhanced the presence of R-spondins in the CM, and confirmed their nature as secreted proteins (FIG. 2B). Addition of sodium chlorate, an inhibitor of sulfation, also increased the level of R-spondin proteins in CM (Nam, et al., unpublished data). These results raise the possibility that secreted R-spondins may be associated, in part, with the heparin sulfate proteoglycan (HSPG) of the plasma membrane and extracellular matrix.

R-spondin is Heparin-binding Protein

Figure 3:
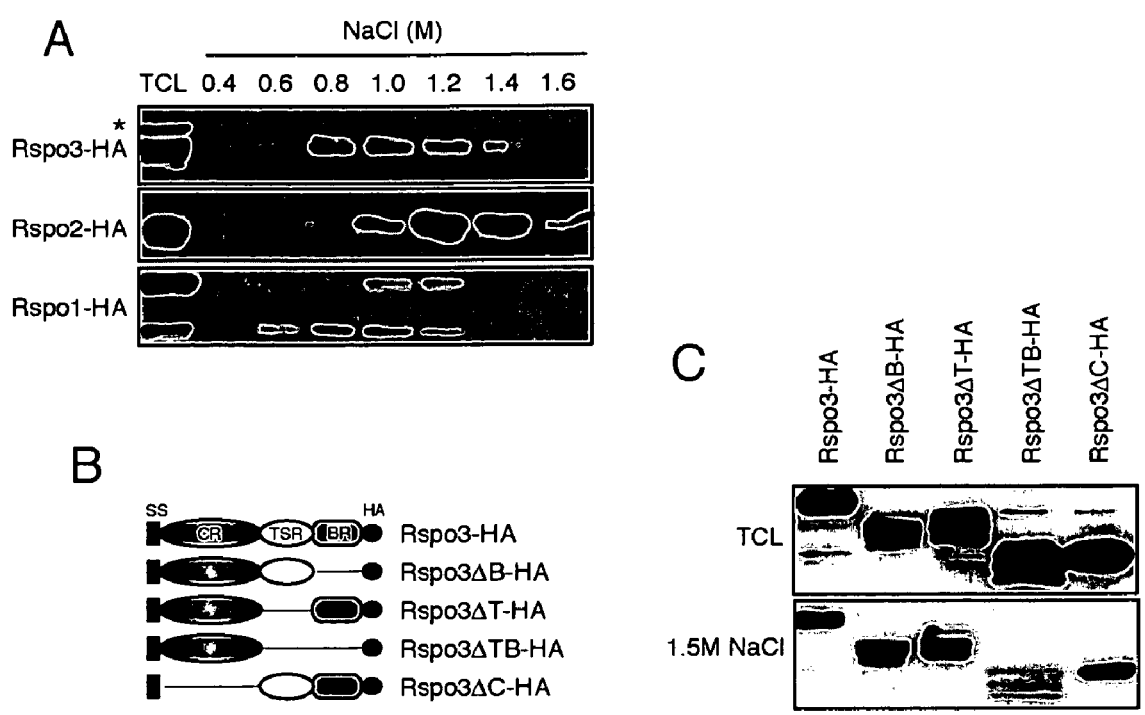
FIG. 3 shows the R-spondins are heparin-binding proteins. (A) SDS-polyacrylamide gels of total cell lysates (TCL) containing HA-tagged R-spondin proteins. (B) Schematic diagram of R-spondin3-HA deletion constructs. (C) SDS-polyacrylamide gels of TCL containing various R-spondin3 deletion constructs.

It was next examined whether R-spondin protein can bind to heparin. Lysates were prepared from the 293T cells transfected with R-spondin-HA expression plasmids. The cell lysates were incubated with heparin-sepharose beads, and the bound proteins were eluted with a series of buffers with increasing salt concentrations. All R-spondins tested efficiently bound to the heparin-sepharose beads, and were eluted from the heparin beads between 0.8 and 1.2M NaCl concentrations (FIG. 3A). Thus, all R-spondins bind to heparin with an affinity comparable to that of FGFs (fibroblast growth factor) (Adams, J. C., and Tucker, R. P. (2000) Dev Dyn 218:280-299).

In order to determine which domains within R-spondin3 are required for heparin binding, a set of R-spondin3 constructs containing various deletions of the identified domains were generated (FIG. 3B). Total lysates of 293T cells transfected with these constructs were prepared, and the heparin binding of each protein construct was determined. It appears that both basic and TSR domains contains most of heparin binding capability as deletion of both domains significantly decreased R-spondin3 binding to heparin (FIG. 3C). In contrast, R-spondin3 with CR domain deletion showed an efficient binding to heparin comparable to that of wild type R-spondin3, indicating that the CR domain is not necessary for heparin binding. It was conclude that R-spondin3 is a heparin-binding protein, and both TSR and BR domains are necessary for this binding.

R-spondin Activates Canonical Wnt/β-catenin Signaling

Figure 4:
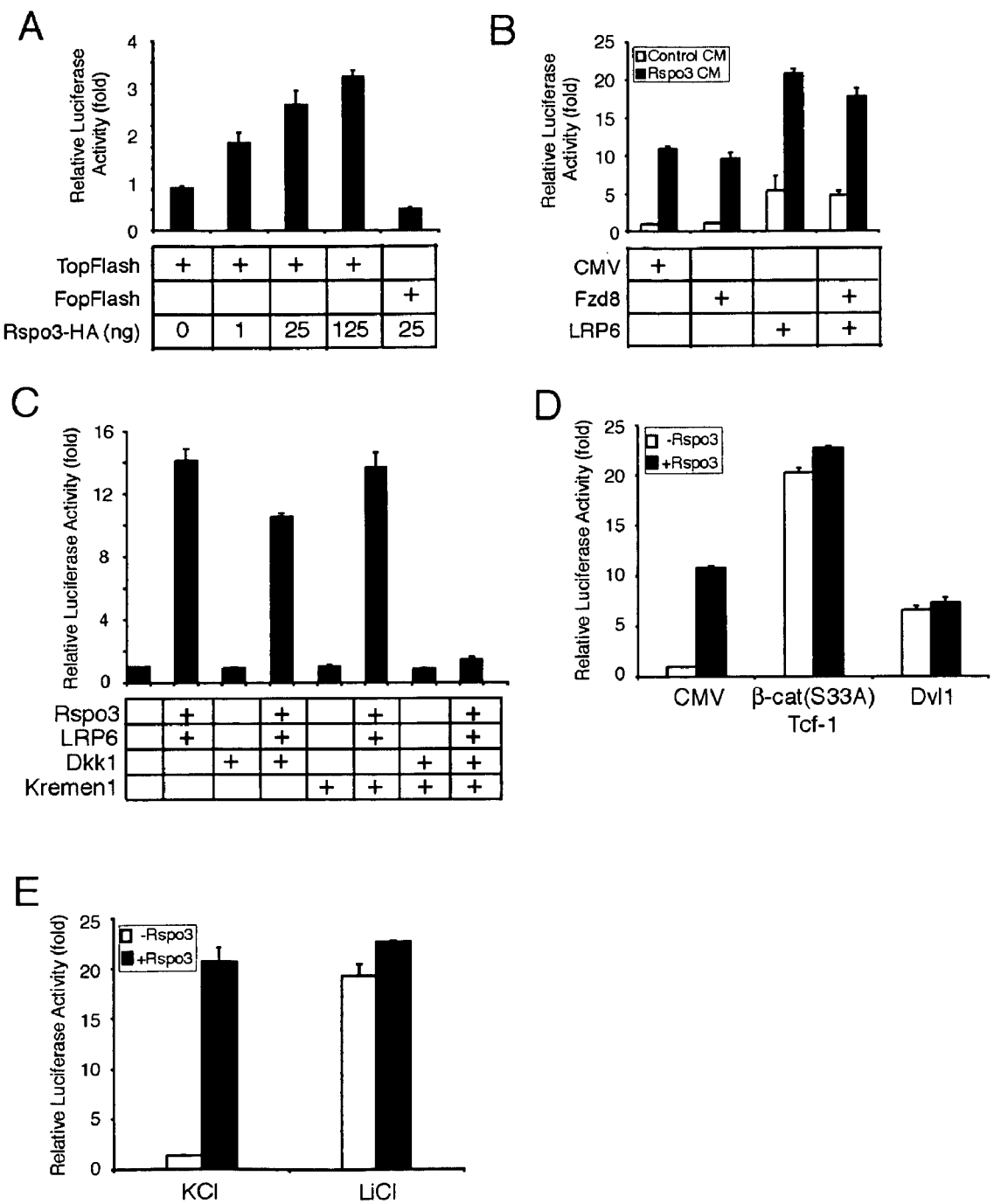
FIG. 4 shows that R-spondins activate Wnt/β-catenin signaling. (A) Mouse R-spondin3 induced β-catenin-dependent gene activation in a dose-dependent manner. (B) R-spondin functions at the receptor level. (C) Dkk1 and Kremen1 reversed the activation of the TopFlash reporter that was induced by both R-spondin3 and LPR6. (D) No synergy was shown between R-spondin3 and intracellular components of the Wnt signaling pathway. (E) Cristin1/R-spondin3 failed to potentiate the TopFlash reporter activation induced in 293T cells by the treatment of LiC1, an inhibitor of GSK3β.

Two observations led us to evaluate the possible involvement of R-spondin in Wnt signaling. First, embryonic expression of R-spondins highly overlaps with known Wnt gene expression domains (Takada, S., et al. (1994) Genes Dev 8:174-189). Second, CCN (Cyr61/CTGF/Nov) family proteins, which contain structurally similar domains to those of R-spondins such as the cysteine-rich and TSR domains (Brigstock, D. R. (2003) J Endocrinol 178:169-175), were recently demonstrated to either antagonize or agonize Wnt signaling in a context-dependent manner (Mercurio, S., et al. (2004) Development 131:2137-2147; Latinkic, B. V., et al. (2003) Development 130:2429-2441). The steady-state level of β-catenin protein, and the activity of reporter constructs such as the TopFlash reporter carrying TCF1 binding sites in their upstream regulatory region, were extensively used to analyze canonical Wnt signaling. In 293T cells, over-expression of R-spondin3 strongly induced TopFlash reporter activity in a dose-dependent manner (FIG. 4A). Activation was dependent on the TCF1 binding site, since a reporter carrying non-functional TCF1 binding sites (FopFlash) was not activated by R-spondin3. In addition, other mouse R-spondin family members, and Xenopus homologs showed similar activities (Nam, et. al., unpublished data; Kazanskaya, O., et al. (2004) Dev Cell 7:525-534)). Interestingly, conditioned media collected from the culture of 293T cells transfected with R-spondins effectively induced TopFlash reporter activity, suggesting that R-spondin may act in the extracellular environment (FIG. 4B).

To determine the target position for R-spondin activity in the Wnt signaling axis, reporter activity was examined under the conditions of R-spondin3 co-expressed with various Wnt signaling components. R-spondin3 activity was synergistically potentiated by the LRP6 receptor (FIG. 4B). However, R-spondin3, unlike Wnt ligands, failed to show any significant synergy with Fzd8 (FIG. 4B). Fzd8 also failed to further enhance the reporter activity co-induced by R-spondin3 and LRP6 (FIG. 4B). Therefore, Fzd8 does not appear to actively contribute to the intracellular transmission of R-spondin signals. Furthermore, the reporter activity induced by both LRP6 and R-spondin3 was highly sensitive to the combined presence of both Dickkopf1 (Dkk1) (Glinka, A., et al. (1998) Nature 391:357-362) and Kremen1(Mao, B., et al. (2002) Nature 417:664-667), a condition that presumably enhances LRP6 receptor endocytosis, and inhibits intracellular signaling through the LRP6 receptor (Mao, B., et al. (2002) Nature 417:664-667) (FIG. 4C). However, Dkk1 or Kremen1 alone marginally affected or had no effect on reporter activity induced by R-spondin3 and LRP6.

In contrast, R-spondin3 failed to show any synergistic activation of the reporter when co-expressed with other intracellular components of Wnt signaling, including Dvl1 or β-catenin/TCF1 (FIG. 4D). In addition, when cells were treated with Lick, which mimics Wnt activation by inhibiting GSK3β, no synergistic activation with R-spondin3 on reporter activity was observed (FIG. 4E).

R-spondin Stabilizes Endogenous β-catenin, and Induces Genes Known as Canonical Wnt/β-catenin Targets R-spondin activity was examined on stabilization of β-catenin, a landmark intracellular event upon activation of canonical Wnt signaling. Consistent with the reporter assay results, R-spondin1 and 3 CM effectively increased the steady-state β-catenin level in 293T cells similar to Wnt3a CM (FIG. SA). This result clearly suggests that degradation of cytoplasmic β-catenin is prevented by R-spondins, and accumulated β-catenin may lead to the activation of TopFlash reporter activity (FIG. 4A).

Figure 5:
FIG. 5 shows the induction of canonical Wnt signaling target genes by R-spondin3. (A) Shows the stabilization of β-catenin proteins by R-spondins. (B) Shows the induction of Wnt3a target genes by R-spondin2 in P19 embryonic carcinoma cells. (C) Shows the induction of Wnt target genes in *Xenopus* animal cap explants injected with mouse R-spondin3 RNA.

It was further determined whether R-spondin can induce the expression of genes known as canonical Wnt signaling targets. P19 mouse embryonic carcinoma cells were stimulated with Wnt3a or R-spondin3 CM for one and two days, and expression of BrachyuryT and Cdx1, two known Wnt3a target genes, were examined by semi-quantitative RT-PCR. Robust induction of both genes was observed in the cells incubated with R-spondin3 and Wnt3a CM (FIG. 5B). Since both genes are expressed in the tailbud region of mouse embryos (Subramanian, V., Meyer, B. I., and Gruss, P. (1995) Cell 83:641-653; Wilkinson, D. G., Bhatt, S., and Herrmann, B. G. (1990) Nature 343:657-659), where R-spondin3 is also expressed, it is very likely that both BrachyuryT and Cdx1 are the direct down-stream targets for R-spondin3 signaling.

Axis duplication assay in Xenopus embryos is a signature assay to test Wnt/β-catenin activation in vivo. Ectopic R-spondin expression was next examined in Xenopus embryos to determine whether it induces axis duplication. Injection of up to 5 ng of R-spondin1 and R-spondin3 RNA into one of the ventral blastomeres at 4-cell stage embryos did not induce any significant axis duplication, while similarly injected Wnt1 RNA in picogram quantity produced clear axis duplication (data not shown). Our results are consistent with those recently reported with Xenopus R-spondin genes (Kazanskaya, O., et al. (2004) Dev Cell 7:525-534). The majority of embryos injected with high concentration of R-spondin3 RNA displayed severe gastrulation defects. Additionally, tail duplication was occasionally observed in a small number of the R-spondin3 RNA-injected embryos. Interestingly, unlike whole embryo injection, transcription of two known Wnt target genes, Siamois and Xnr3, was significantly enhanced in Xenopus animal cap explants injected with mouse R-spondin3 RNA as compared to uninjected control cap explants (FIG. 5C). Taken together, it was conclude that the R-spondin family of proteins possesses signaling activities that induce β-catenin-dependent gene activation.

Binding of R-spondin to the Extracellular Domains of Fzd8 and LRP6 Receptors

Figure 6:
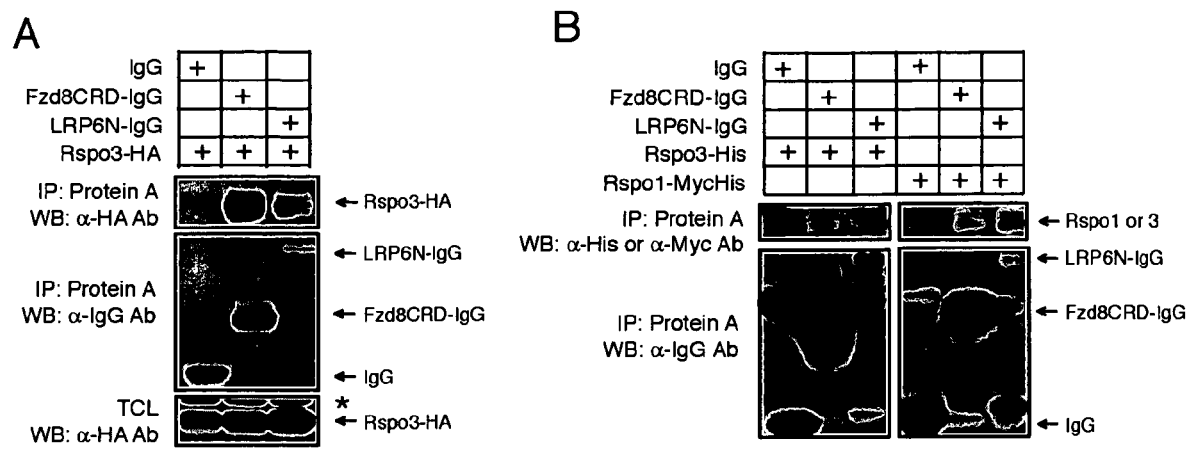
FIG. 6 shows that R-spondin physically interacts with the extracellular domains of the Fzd8 and LRP6 receptors. (A) Shows the interaction of R-spondin3 with mouse Fzd8 and human LRP6 in cells. (B) Shows cell-free interaction of R-spondins with the Fzd8 or LRP6 receptors.

To biochemically characterize R-spondin activity at the Fzd/LRP receptor complexes, it was examined whether R-spondin3 binds to the extracellular domain of Fzd8, LRP6 or both. First, a co-transfection/co-immunoprecipitation format was utilized. Expression plasmids encoding mouse R-spondin3 (tagged with the HA epitope), human immunoglobin Fc fusion forms of the cysteine-rich domain (CRD) of mouse Fzd8 (Fzd8CRD-IgG) (Hsieh, J. C., et al. (1999) Proc Natl Acad Sci USA 96:3546-3551), and the extracellular domain of human LRP6 (LRP6N-IgG) (Tamai, K., et al. (2000) Nature 407:530-535), were co-transfected into 293T cells. Cell lysates were subjected to immunoprecipitation followed by western blot analysis. The R-spondin3 protein was effectively co-immunoprecipitated with Fzd8 CRD- and LRP6N-IgG but not IgG (FIG. 6A). The LRP6N-IgG protein, although much less concentrated than Fzd8CRD-IgG, co-immunoprecipitated a comparable amount of R-spondin3. Thus, R-spondin3 may bind to the LRP6 ectodomain at a higher affinity than the CRD of Fzd8 in cells.

These interactions were next examined in cell-free liquid phase conditions. Histidine-tagged R-spondin1 and 3 proteins were isolated from total lysates of 293T cells transiently transfected with R-spondin expression plasmids. Both isolated R-spondins effectively activated TopFlash reporter, indicating they are biologically active (data not shown). IgG fusion forms of Fzd8CRD and LRP6N were prepared as CM as described previously (Tamai, K., et al. (2000) Nature 407: 530-535). It was found that both R-spondin1 and 3 were specifically co-precipitated with Fzd8CRD-IgG and LRP6N-IgG, but not with IgG under these conditions (FIG. 6B). Similar to the co-transfection/co-immunoprecipitation results, R-spondin proteins appears to bind to LRP6N-IgG more efficiently than FzdCRD-IgG, as similar amount of R-spondins were co-immunoprecipitated with a much reduced amount of LRP6N-IgG.

Figure 7:
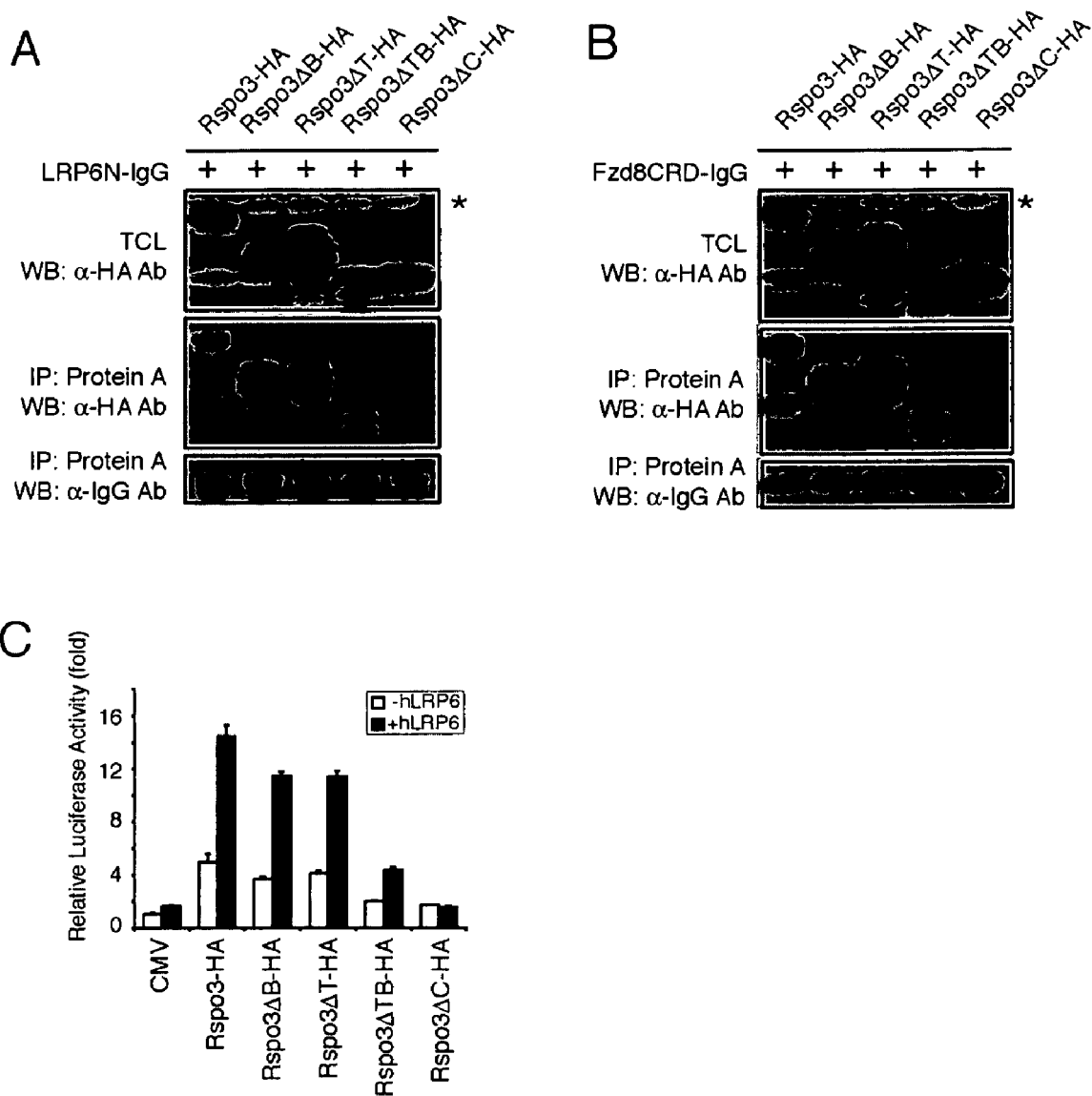
FIG. 7 shows the cysteine-rich (CR) domain of R-spondin3 in a primary interacting domain with the Fz8/LRP6 receptor complex. (A) 293T cells were co-transfected with expression plasmid encoding LRP6-IgG and R-spondin3 derivatives carrying various deletions. (B) 293T cells were co-transfected with expression plasmids encoding Fz8CRD-IgG and R-spondin3 derivatives carrying various deletions. (C) The CR domain of R-spondin3 mediates a synergistic activation of β-catenin-dependent gene activation by LRP6 and R-spondin3.

To further determine which domain of R-spondin3 is involved in these interactions, R-spondin3 deletion mutants were co-transfected with Fzd8 CRD-IgG or LRP6N-IgG, and analyzed their interactions. It was determined that the CR domain of R-spondin3 was essential for the interaction with both Fzd8 and LRP6 receptors (FIG. 7A and B). Consistent with co-immunoprecipitation results, R-spondin3 construct lacking its CR domain failed to signal through the LRP6 receptor in the reporter assay (FIG. 7C).

R-spondin Positively Modulates Wnt Ligand Activity

Figure 8:
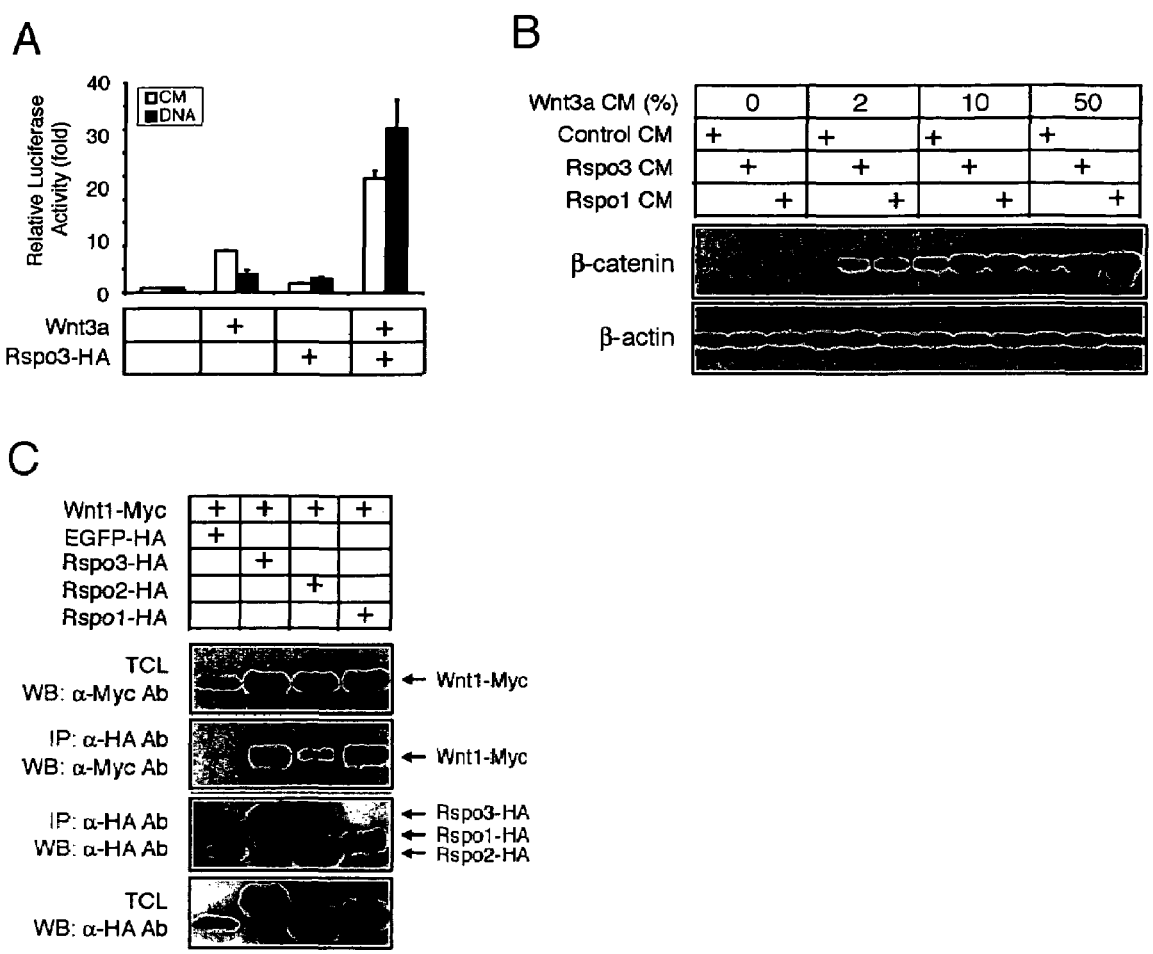
FIG. 8 shows R-spondin proteins function as a positive modulator of Wnt ligand. (A) Shows R-spondin3 and Wnt3a CM synergistically induce TopFlash reporter activity. (B) Shows a synergistic increase of steady-state level of β-catenin protein in mouse L-cells stimulated with various concentrations of Wnt3a, R-spondin3 CM or both for 12 hours. (C) Shows that Wnt1 and R-spondins are associated with each other in 293T cells.
Figure 9:
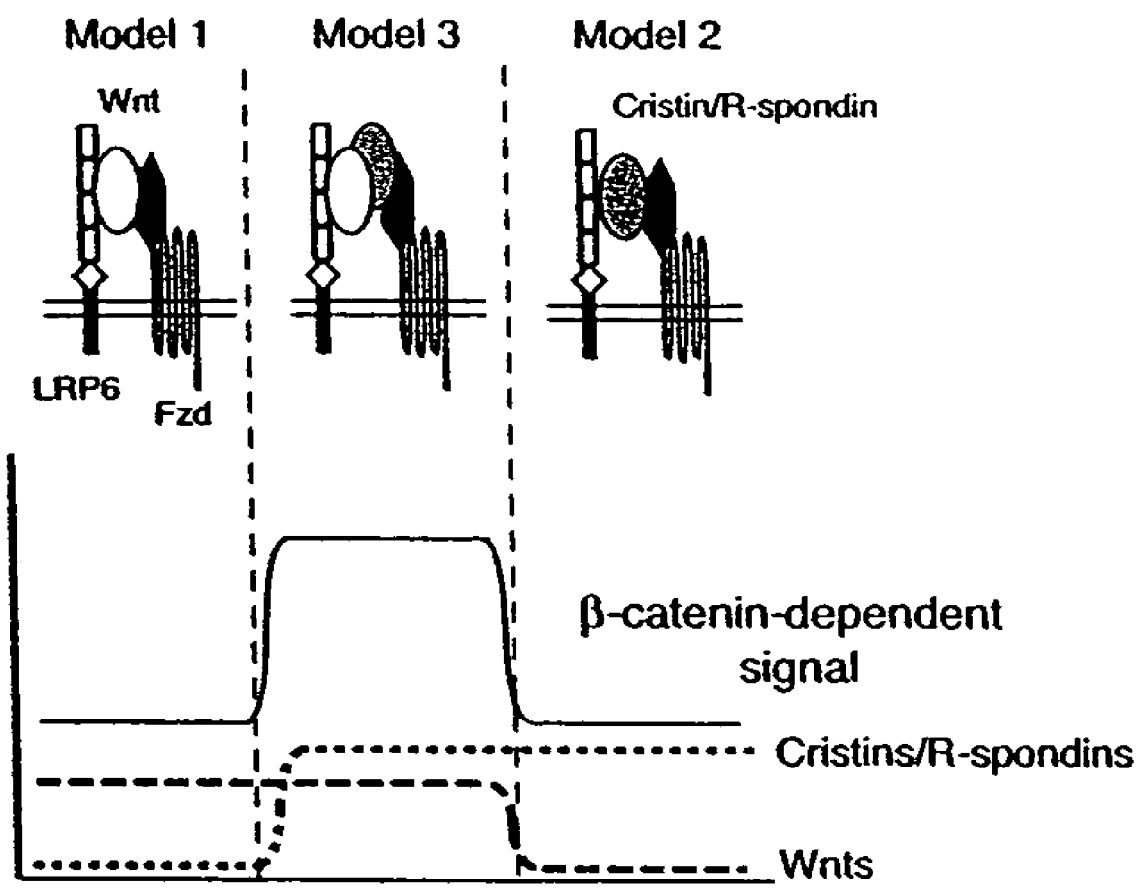
FIG. 9 shows proposed models for R-spondin and Wnt signaling through the Fz/LRP6 receptor complex. Model 1 is a current view of canonical Wnt signaling. In model 2, R-spondins generate β-catenin-dependent signaling. In contrast, when R-spondin and Wnt co-exist, very high level of β-catenin signaling activity is produced (model 3). Wnt and R-spondin ligands are indicated by white and gray oval shapes, respectively.

Unexpectedly, it was observed that co-transfection of canonical Wnts, such as Wnt1 and Wnt3a, and R-spondin3 also induced TopFlash reporter activity at a significantly higher level than either Wnt or R-spondin3 alone (FIG. 8A). R-spondins1, 2, and 4 showed similar synergistic activities with Wnts on the induction of reporter activity (Nam et. al., unpublished data). Both R-spondin-containing CM and DNA-mediated transfection formats generated similar synergistic activation by R-spondin3 and Wnt3a (FIG. 8A), which indicates that synergistic activation of Wnt signaling by R-spondin occurs in the extracellular environment. The steady-state level of β-catenin protein in mouse L-cells was examined after exposure to Wnt3a CM, R-spondin CM or a mixture of Wnt3a and R-spondin CM. Consistent with reporter assay results, stimulation of cells with both R-spondin and Wnt3a synergistically enhanced β-catenin stability (FIG. 8B). Similar synergistic activation of signaling was also observed in the activation of Siamois and Xnr3 gene transcription in *Xenopus* animal cap explants (FIG. 5C).

To investigate the biochemical nature of the synergistic activity between R-spondin and Wnts, it was examined whether Wnt1 and R-spondin proteins physically interact with each other in cultured cells. In the lysates of 293T cells co-transfected with Wnt1-Myc and R-spondin-HA expression plasmids, Wnt proteins were efficiently co-immunoprecipitated with R-spondin1, 2, and 3 proteins (FIG. 8C). Among the tested R-spondins, R-spondin2 seems to be co-immunoprecipitated with Wnt1 less effectively than R-spondin1 and 3. Thus, R-spondins appear to be physically associated with Wnts, possibly through a direct interaction.

We claim:

1. A composition comprising an isolated agent consisting of the Cristin1/R-spondin3 amino acid sequence of SEQ ID NO: 1.

2. The composition of claim 1 further comprising Wnt protein.

3. A method for activating Wnt signaling, the method comprising:
   a) providing at least one cell in which activation of Wnt signaling is desired; and
   b) contacting the cell with a composition comprising an isolated agent consisting of the Cristin1/R-spondin3 amino acid sequence of SEQ ID NO: 1.

4. The method of claim 1 wherein the cell is a stem cell.

5. The method of claim 1 wherein contact of the cell with the isolated agent results in an activation of $\beta$-catenin/TCF-dependent gene expression.

6. The method of claim 1 wherein the cell is selected from the group consisting of murine, chicken, *Xenopus*, zebrafish, and human.

7. The method of claim 1 wherein the cell is further contacted with an exogenous Wnt protein.

8. The method of claim 7 wherein the Wnt protein is Wnt1 or Wnt3a.

* * * * *

SEQUENCE LISTING

<160> NUMBER OF SEQ ID NOS: 18

<210> SEQ ID NO 1
<211> LENGTH: 277
<212> TYPE: PRT
<213> ORGANISM: Mus musculus

<400> SEQUENCE: 1

Met His Leu Arg Leu Ile Ser Cys Phe Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Val
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

```
Lys Cys Lys Val Asp Cys Asp Thr Cys Phe Asn Gln Asn Phe Cys Thr
            100                 105                 110

Lys Cys Lys Ser Gly Phe Tyr Leu His Leu Gly Lys Cys Leu Asp Ser
            115                 120                 125

Cys Pro Glu Gly Leu Glu Ala Asn Asn His Thr Met Glu Cys Val Ser
            130                 135                 140

Ile Val His Cys Glu Ala Ser Glu Trp Ser Pro Trp Ser Pro Cys Met
145                 150                 155                 160

Lys Lys Gly Lys Thr Cys Gly Phe Lys Arg Gly Thr Glu Thr Arg Val
            165                 170                 175

Arg Asp Ile Leu Gln His Pro Ser Ala Lys Gly Asn Leu Cys Pro Pro
            180                 185                 190

Thr Ser Glu Thr Arg Thr Cys Ile Val Gln Arg Lys Cys Ser Lys
            195                 200                 205

Gly Glu Arg Gly Lys Lys Gly Arg Glu Arg Lys Arg Lys Lys Leu Asn
            210                 215                 220

Lys Glu Glu Arg Lys Glu Thr Ser Ser Ser Asp Ser Lys Gly Leu
225                 230                 235                 240

Glu Ser Ser Ile Glu Thr Pro Asp Gln Gln Glu Asn Lys Glu Arg Gln
            245                 250                 255

Gln Gln Gln Lys Arg Arg Ala Arg Asp Lys Gln Lys Ser Val Ser
            260                 265                 270

Val Ser Thr Val His
            275

<210> SEQ ID NO 2
<211> LENGTH: 243
<212> TYPE: PRT
<213> ORGANISM: Mus musculus

<400> SEQUENCE: 2

Met Arg Phe Cys Leu Phe Ser Phe Ala Leu Ile Ile Leu Asn Cys Met
1               5                   10                  15

Asp Tyr Ser Gln Cys Gln Gly Asn Arg Trp Arg Arg Asn Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
            85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
            115                 120                 125

Pro Asp Gly Phe Ala Pro Leu Asp Glu Thr Met Glu Cys Val Glu Gly
            130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
            165                 170                 175

Val Lys Lys Pro Ala Lys Asp Thr Ile Pro Cys Pro Thr Ile Ala Glu
```

-continued

```
                180                 185                 190
Ser Arg Arg Cys Lys Met Ala Met Arg His Cys Pro Gly Gly Lys Arg
            195                 200                 205

Thr Pro Lys Ala Lys Glu Lys Arg Asn Lys Lys Arg Arg Lys Leu
    210                 215                 220

Ile Glu Arg Ala Gln Glu Gln His Ser Val Phe Leu Ala Thr Asp Arg
225                 230                 235                 240

Val Asn Gln

<210> SEQ ID NO 3
<211> LENGTH: 265
<212> TYPE: PRT
<213> ORGANISM: Mus musculus

<400> SEQUENCE: 3

Met Arg Leu Gly Leu Cys Val Val Ala Leu Val Leu Ser Trp Thr His
  1               5                  10                  15

Ile Ala Val Gly Ser Arg Gly Ile Lys Gly Lys Arg Gln Arg Ile
                20                  25                  30

Ser Ala Glu Gly Ser Gln Ala Cys Ala Lys Gly Cys Glu Leu Cys Ser
            35                  40                  45

Glu Val Asn Gly Cys Leu Lys Cys Ser Pro Lys Leu Phe Ile Leu Leu
        50                  55                  60

Glu Arg Asn Asp Ile Arg Gln Val Gly Val Cys Leu Pro Ser Cys Pro
 65                 70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Gln Glu Ala Leu Tyr Leu His Lys Gly Arg Cys Tyr Pro Ala
        115                 120                 125

Cys Pro Glu Gly Ser Thr Ala Ala Asn Ser Thr Met Glu Cys Gly Ser
130                 135                 140

Pro Ala Gln Cys Glu Met Ser Glu Trp Ser Pro Trp Gly Pro Cys Ser
145                 150                 155                 160

Lys Lys Arg Lys Leu Cys Gly Phe Arg Lys Gly Ser Glu Glu Arg Thr
                165                 170                 175

Arg Arg Val Leu His Ala Pro Gly Gly Asp His Thr Thr Cys Ser Asp
            180                 185                 190

Thr Lys Glu Thr Arg Lys Cys Thr Val Arg Arg Thr Pro Cys Pro Glu
        195                 200                 205

Gly Gln Lys Arg Arg Lys Gly Gln Gly Arg Glu Asn Ala Asn
    210                 215                 220

Arg His Pro Ala Arg Lys Asn Ser Lys Glu Pro Arg Ser Asn Ser Arg
225                 230                 235                 240

Arg His Lys Gly Gln Gln Gln Pro Gln Pro Gly Thr Thr Gly Pro Leu
                245                 250                 255

Thr Ser Val Gly Pro Thr Trp Ala Gln
            260                 265

<210> SEQ ID NO 4
<211> LENGTH: 228
<212> TYPE: PRT
<213> ORGANISM: Mus musculus

<400> SEQUENCE: 4
```

Met Arg Ala Pro Leu Cys Leu Leu Leu Leu Ala His Ala Val Asp
 1               5                  10                  15

Met Leu Ala Leu Tyr Arg Arg Lys Lys Gln Ala Gly Thr Gly Leu Gly
             20                  25                  30

Gly Asn Cys Thr Gly Cys Val Ile Cys Ser Glu Glu Asn Gly Cys Ser
         35                  40                  45

Thr Cys Gln Gln Arg Leu Phe Leu Phe Ile Arg Arg Glu Gly Ile Arg
     50                  55                  60

Gln Tyr Gly Lys Cys Val His Asp Cys Pro Leu Gly Phe Phe Gly Ile
 65                  70                  75                  80

Arg Gly Gln Glu Ala Asn Arg Cys Lys Lys Cys Gly Ala Thr Cys Glu
             85                  90                  95

Ser Cys Phe Ser Gln Asp Phe Cys Ile Arg Cys Lys Arg Arg Phe His
         100                 105                 110

Leu Tyr Lys Gly Lys Cys Leu Pro Ser Cys Pro Pro Gly Thr Leu Thr
     115                 120                 125

His Gln Ser Thr Arg Glu Cys Gln Glu Glu Cys Glu Pro Ser Pro Trp
 130                 135                 140

Gly Ser Trp Ser Pro Cys Ile His Asn Gly Lys Thr Cys Gly Ser Gly
145                 150                 155                 160

Trp Gly Leu Glu Thr Arg Val Arg Glu Ala Gly Pro Ala Lys Gln Glu
                 165                 170                 175

Glu Thr Ala Ser Cys Arg Val Leu Ser Glu Ser Arg Lys Cys Pro Ile
             180                 185                 190

Lys Arg Leu Cys Pro Gly Glu Arg Asn Pro Arg Gln Lys Asn Arg Lys
         195                 200                 205

Asp Arg Arg Gln Arg Lys Asp Arg Lys Leu Glu Arg Arg Pro His Gln
     210                 215                 220

Arg Gly Ser Gln
225

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggcaaagt ggagattgtt gcc                                            23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatgatgacc cgtttggctc c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 7
gtacactgtg aggccagtga a                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atggctagaa cacctgtcct g                                              21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgctgcctgt gagtcatac                                                 19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acaagaggct gtagaacatg                                                20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaccaagga caagtaccgt g                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtagaaact cctccttgac g                                              21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 13
aaggaacccc accaggataa                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tactggtggc tggagaaata                                               20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tccacttgtg cagttccaca g                                             21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atctcttcat ggtgcctcag g                                             21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtggaaagcg acgaagactc                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgagctcga gtagttggac                                               20
```